United States Patent [19]

Bertleff et al.

[11] Patent Number: 4,999,443
[45] Date of Patent: Mar. 12, 1991

[54] TRANSITION METAL COMPLEXES

[75] Inventors: Werner Bertleff, Viernheim; Dieter Koeffer, Weinheim, both of Fed. Rep. of Germany; Wolfgang Kläui, Vaals, Netherlands; Choong-Eui Song, Seoul, Rep. of Korea

[73] Assignee: BASF Aktiengesellschaft, Ludwigshafen, Fed. Rep. of Germany

[21] Appl. No.: 360,863

[22] Filed: Jun. 2, 1989

[30] Foreign Application Priority Data

Jun. 8, 1988 [DE] Fed. Rep. of Germany ....... 3819487

[51] Int. Cl.$^5$ .................... C07F 15/00; C07F 15/08; C07F 9/66; C07F 1/00
[52] U.S. Cl. .................................. 556/136; 556/13; 556/30; 556/138; 556/28; 556/110; 568/454; 568/455
[58] Field of Search ....................... 556/136, 2, 13, 30, 556/28, 138, 110; 568/8, 11, 454, 455

[56] References Cited

U.S. PATENT DOCUMENTS

| | | | |
|---|---|---|---|
| 4,248,802 | 2/1981 | Kuntz et al. | 568/454 |
| 4,523,036 | 6/1985 | Cornils et al. | 568/454 |
| 4,740,626 | 4/1988 | Bahrmann et al. | 568/454 |
| 4,812,587 | 3/1989 | Fiedler et al. | 556/136 |
| 4,873,349 | 10/1989 | Robin et al. | 556/136 X |
| 4,885,401 | 12/1989 | Billig et al. | 568/454 |

OTHER PUBLICATIONS

Kläui et al., Angew. Chem. 97 (1985), 697(=Angew. Chem. Int. Ed. 24, 683(1985).
Kläui et al., Chem. Ber./115 (1982), 1922.
J. Organometal Chem. 331 (1987), 317.
Kläui, Z. Naturforsch. 34B (1979), 1403.
Schleman et al., J. Organometal Chem. 323 (1987), 103.
Werner et al., Z. Anorg. Allg. Chem. 458 (1979), 301.
Houben–Weyl, Methoden der Organischen Chemie, vol. XII/2, pp. 53–73, Thieme, Stuttgart, 1964.
Brauer, Handbuch der Präparativen Anorganischen Chemie, Enke, 3rd Edition, vol. 3, Stuttgart, 1981.
Houben–Weyl, Methoden der Organischen Chemie, vol. XII/1, pp. 247–261, Thieme, Stuttgart, 1964.

Primary Examiner—Arthur C. Prescott
Attorney, Agent, or Firm—John H. Shurtleff

[57] ABSTRACT

Transition metal complexes of the general formula I $$[A]^{x-} [Q]^{+}_{x} \qquad \text{I}$$

where Q is one equivalent of a cation, x is from 0 to 2 and A is a transition metal complex of the general formula

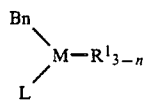

A where n is from 1 to 3, M is positively charged cobalt, rhodium, iridium or ruthenium, the ligands B are phosphonic, arsonic, phosphinic and/or arsinic acid ligands which are esterified with identical or different alcohols, one or more of these alcohol components carrying a functional group, L is

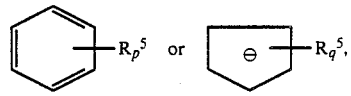

the radicals $R^5$ are identical or different radicals from the group consisting of $C_1$–$C_4$-alkyl and phenyl, p is an integer from 0 to 6, q is an integer from 0 to 5, and $R^1$ is fluorine, chlorine, bromine, iodine, cyanide, isocyanide, cyanate, isocyanate, thiocyanate, isothiocyanate, $C_1$–$C_4$-alkyl, $C_1$–$C_4$-trialkyl phosphite or triaryl phosphite, are used as catalysts, or prepared in situ, in processes for the cyclotrimerization of acetylene compounds, for the catalytic hydrogenation of unsaturated compounds and for the hydroformylation of alkenes.

7 Claims, No Drawings

TRANSITION METAL COMPLEXES

The present invention relates to novel transition metal complexes of the general formula I

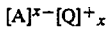

where Q is one equivalent of a cation, x is from 0 to 2 and A is a transition metal complex of the general formula

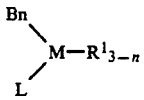

where n is from 1 to 3, M is positively charged cobalt, rhodium, iridium, or ruthenium, the groups B are identical or different groups of the general formula II

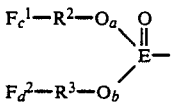

where E is phosphorus or arsenic, O is oxygen, $R^2$ and $R^3$ are each $C_1$-$C_{20}$-alkylene which in turn may carry up to two cycloalkyl, heterocycloalkyl, aryl or hetaryl groups having a total of not more than 15 ring atoms, and $R^2$ and $R^3$ may be interrupted by oxygen, sulfur or (—$NR^4$), $R^4$ is hydrogen or $C_1$-$C_4$-alkyl and the heteroatoms or heteroatom groups are each separated by two or more carbon atoms and the radicals $R^4$ derived from two different (—$NR^4$) groups may furthermore be bonded to one another to form a 5-membered or 6-membered ring, $F^1$ and $F^2$ are each alkenyl, alkynyl, $C_5$-$C_{12}$-cycloalkadienyl, nitrile, amino, $C_1$-$C_4$mono- and dialkylamino, $C_1$-$C_4$-acyl, hydroxyl, $C_1$-$C_4$-alkoxy, aryloxy, $C_1$-$C_4$-alkylsulfido, arylsulfido, $C_1$-$C_4$-dialkyl and and diarylphosphido and/or carboxylato, a-d are each 0 or 1, with the proviso that a+b>0 and c+d>0, L is

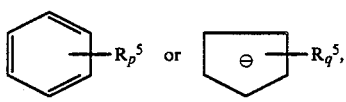

the radicals $R^5$ are identical or different radicals from the group consisting of $C_1$-$C_4$-alkyl and phenyl, p is an integer from 0 to 6 and q is an integer from 0 to 5, and $R^1$ is fluorine, chlorine, bromine, iodine, cyanide, isocyanide, cyanate, isocyanate, thiocyanate, isothiocyanate, $C_1$-$C_4$-alkyl, $C_1$-$C_4$-trialkyl phosphite or triaryl phosphite.

The present invention furthermore relates to a process for the catalytic hydrogenation of unsaturated compounds, for the hydroformylation of alkenes and for the cyclotrimerization of acetylene compounds, these transition metal complexes being used as catalysts or being produced in situ.

Homogeneous transition metal catalysts have become very important in the processes of industrial organic chemistry over the past few years, in particular in hydrogenation and hydroformylation processes. However, when these homogeneous catalysts are used, the problem of product isolation with retention of catalyst activity still presents considerable difficulties. In particular, homogeneous catalysts which contain a transition metal as the active component are frequently unstable under the conditions under which the reaction mixture is worked up, so that the catalyst is partially deactivated during this procedure. Furthermore, complete separation of the often expensive, noble metal-containing homogeneous catalysts from the product is difficult to achieve. Consequently, working up of the reaction mixture results in losses due to the catalyst being discharged with the product.

In the past, attempts have therefore been made to fix a catalyst by means of suitable ligands, for example sulfonated phosphines, in a liquid phase which is immiscible with the product-containing liquid phase. In this procedure, the product is isolated as described in DE-B 26 27 354, EP-B 103 810 and DE-A 35 34 314, by phase separation. Although this substantially avoids subjecting the catalyst to high temperatures during working up, the catalyst is still deactivated during working up, owing to the elimination of the fulfo groups of the cleavage of the phosphorus/aryl bond.

It is an object of the present invention to provide transition metal complexes which are suitable as homogeneous catalysts for the hydrogenation of unsaturated compounds, for the hydroformylation of alkenes and for the cyclotrimerization of acetylene compounds or for the preparation of these catalysts. These catalysts should have good catalytic activity and high heat stability and should be chemically stable under the conditions under which the reaction mixture is worked up. Furthermore, it should be easy to vary the chemical structure of these transition metal compounds in order to permit them to be used in water or polar or nonpolar organic solvents, as required.

We have found that this object is achieved by novel transition metal complexes of the general formula I

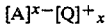

where Q is one equivalent of a cation, x is from 0 to 2 and A is a transition metal complex of the general formula

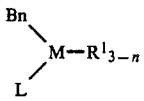

where n is from 1 to 3, M is positively charged cobalt, rhodium, iridium or ruthenium, the groups B are identical or different groups of the general formula II

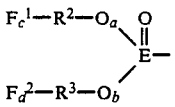

where E is phosphorus or arsenic, O is oxygen, $R^2$ and $R^3$ are each $C_1$-$C_{20}$-alkylene which in turn may carry up to two cycloalkyl, heterocycloalkyl, aryl or hetaryl groups having a total of not more than 15 ring atoms, and $R^2$ and $R^3$ may be interrupted by oxygen, sulfur or (—$NR^4$), $R^4$ is hydrogen or $C_1$-$C_4$-alkyl and the heteroatoms or heteroatom groups are each separated by two or more carbon atoms and the radicals $R^4$ derived from two different (—$NR^4$) groups may furthermore be bonded to one another to form a 5-membered or 6-membered ring, $F^1$ and $F^2$ are each alkenyl, alkynyl, $C_5$-$C_{12}$- cycloalkadienyl, nitrile, amino, $C_1$-$C_4$ mono- and dialkylamino, $C_1$-$C_4$-acyl, hydroxyl, $C_1$-$C_4$-alkoxy, aryloxy, $C_1$-$C_4$-alkylsulfido, arylsulfido, $C_1$-$C_4$-dialkyland and diarylphosphido and/or carboxylato, a–d are each 0 or 1, with the proviso that $a+b>0$ and $c+d>0$, L is

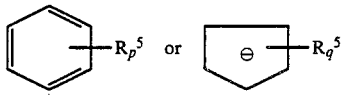

the radicals $R^5$ are identical or different radicals from the group consisting of $C_1$-$C_4$-alkyl and phenyl, p is an integer from 0 to 6 and q is an integer from 0 to 5, and $R^1$ is fluorine, chlorine, bromine, iodine, cyanide, isocyanide, cyanate, isocyanate, thiocyanate, isothiocyanate, $C_1$-$C_4$-alkyl, $C_1$-$C_4$-trialkyl phosphite or triaryl phosphite.

The present invention relates in particular to transition metal complexes of the general formula III $$[L-Co-B_3]^-[Q]^+ \qquad III$$

where E of the group B is phosphorus, transition metal complexes of the general formula III where E of the group II is phosphorus, c is 0 and $R^3$ is $C_1$-$C_{16}$-alkylene, transition metal complexes of the general formula IV

where M is selected from the group consisting of rhodium, iridium and ruthenium cations and E of the group II is phosphorus, and transition metal complexes of the general formula IV where M is selected from the group consisting of rhodium, iridium and ruthenium cations, E of the group II is phosphorus, c is 0 and $R^3$ is $C_1$-$C_{16}$-alkylene.

The present invention furthermore relates to transition metal complexes of the general formula I where $[Q]^+$ is a complex cation of the type V $$[M^Q Z]^{x\oplus} \qquad V$$

where X is 0, 1 or 2, $M^Q$ is rhodium, iridium, ruthenium, chromium, tungsten, molybdenum, manganese, rhenium or copper, Z is one of the bidentate ligands $C_5$-$C_{12}$-cycloalkadiene, $C_4$-$C_8$-alkadiene or a $C_2$-$C_6$-alkylenediphosphido ligand of the general formula VI $$R^6-P-(CH_2)_{1-6}-P-R^6 \qquad VI$$

where $R^6$ is $C_1$-$C_4$-alkyl and/or phenyl, and/or from 1 to 3 identical or different ligands selected from the group consisting of the monodentate ligands carbonyl, nitrosyl, chlorine, bromine, iodine, nitrile, isonitrile, $C_1$-$C_4$-alkyl $C_1$-$C_4$-acyl, $C_1$-$C_4$-alkene, $C_1$-$C_4$-alkyne, $C_1$-$C_4$-trialkylphosphino, triarylphosphino and/or carbyne ligands.

The present invention also relates to transition metal complexes of the general formula I, in which $[Q]^+$ is a complex dication of the general formula VII $$[M^Q-K-M^Q]^{2+} \qquad VII$$

where the ligands K are from 1 to 3 of the bridging ligands from the group consisting of carbonyl, $C_4$-$C_6$-alkadienyl, $C_8$-$C_{12}$-cycloalkadiene, $C_1$-$C_4$-alkylisonitrile, $C_1$-$C_4$-dialkylphosphido, diarylphosphido and/or $C_1$-$C_6$-alkylenediphosphido ligands of the general formula VI.

The present invention furthermore relates to processes for the catalytic hydrogenation of unsaturated compounds, for the hydroformylation of alkenes and for the cyclotrimerization of acetylene compounds, these transition metal complexes being used as catalysts or being produced in situ.

The novel transition metal catalysts of the general formula I $$[A]^{x-}[Q]^+_x \qquad I$$

are composed of a complex A of the general formula

which may be neutral (X=0) or singly or doubly negatively charged, and, where relevant (X>0) a counterion Q, Q being one equivalent of a cation. The central metal ion of these complexes, which may be a cobalt, rhodium, iridium or ruthenium ion of oxidation state II or III, is generally coordinated with four ligands, i.e. L, $R^1$ and B, the ligands L and $R^1$ serving merely for coordinative and electronic saturation of the central ion, while the ligand or ligands B may additionally act as a complexing agent for the cation equivalent Q.

L is an organic ligand which is generally polydentate, for example cyclopentadienyl, monomethylcyclopentadienyl, pentamethylcyclopentadienyl, n-butylcyclopentadienyl, penta-n-butylcyclopentadienyl, phenylcyclopentadienyl, pentaphenylcyclopentadienyl, 1,3,4-triphenylcyclopentadienyl, 1,3,4-triphenyl-2,5-dimethylcyclopentadienyl, benzene, toluene, mesitylene, hexamethylbenzene, hexa-n-butylbenzene, biphenyl or 1,3,5-triphenylbenzene. Any degree of substitution and any substitution pattern of the cyclopentadienyl ligands or alkylbenzene ligands may be chosen. Any degree of substitution and any substitution pattern of the phenyl or phenylalkylbenzene ligands may be chosen, provided that it is not excluded by unfavorable steric interactions between the substituents. Because they are readily available, preferred ligands L are cyclopentadienyl, methylcyclopentadienyl, pentamethylcyclopentadienyl, benzene and hexamethylbenzene. For the transition metal complexes in which A is the complex anion in the general formula III, cyclopentadienyl, methylcyclopentadienyl and pentamethylcyclopentadienyl ligands are particularly preferred. In the case of the transition metal complexes in which A is a complex anion in the general formula IV, benzene ligands and hexamethylbenzene ligands may furthermore prove particularly advantageous. However, it is also possible to use ligands other than those stated here, provided that they are capable of completing the valence shell of the central ion to 16 or 18 electrons.

The number of ligands $R^1$ with which the central ion M is coordinated depends on the number of ligands B. If the central ion is coordinated with 3 ligands B, coordinative and electron saturation of the said ion with a ligand $R^1$ is not necessary. If, on the other hand, only one or two ligands B are coordinated with the central ion M, the presence of 2 ligands $R^1$ or 1 ligand $R^1$ in the complex A is essential for its stability. Since the ligand or ligands $R^1$ serve only for coordinative and electronic saturation of the central atom M, any ligand $R^1$ may be chosen. Examples of the ligands $R^1$ are the groups trialkyl phosphite, triaryl phosphite, $C_1$–$C_4$-alkyl, the halides fluoride, chloride, bromide and iodide and the pseudohalides nitrile, isonitrile, cyanate, isocyanate, thiocyanate and isothiocyanate. However, other ligands may also be used. If, in the complex A, two ligands $R^1$ are coordinated with the central ion, these may of course be identical or different. It is also possible to use one bidentate ligand $R^1$ instead of two monodentate ligands $R^1$.

In contrast to the ligands L and $R^1$, the ligand or ligands B are essential for the catalytic properties of the transition metal complexes I. In the complexes A, which constitute the neutral or anionic part of the transition metal complexes I, the central ion M is coordinated with from 1 to 3, preferably 2 or 3, identical or different ligands B, which are each a group of the general formula II

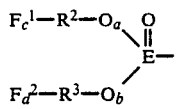

II

Since E may be a phosphorus or arsenic atom, the ligands B may therefore be phosphonic or arsonic esters, if a and b are each 1, or phosphinic or arsinic esters, if a or b is 0, i.e. the phosphorus or arsenic atoms in B may be bonded directly and/or via an oxygen atom to identical or different radicals $R^2$ and $R^3$.

$R^2$ and $R^3$ are each $C_1$–$C_{20}$-alkylene or, if c or d is 0, alkyl. Alkylene groups of 1 to 16 carbon atoms are preferred.

The alkylene groups may in turn carry up to 2 cycloalkyl, heterocycloalkyl, aryl or hetaryl groups as substituents. These ring systems may comprise up to 15 ring atoms.

In principle, all $C_3$–$C_{15}$-cycloalkyl systems may be used as cycloalkyl substituents. The use of cycloalkyl systems having a larger number of members is also possible but has no further advantages with regard to the catalytic activity and the chemical properties of the novel compounds prepared therefrom. The cycloalkyl systems may be monocyclic, fused or bridged. Examples are cyclopropyl, cyclohexyl, decalinyl, indanyl, cyclooctyl and norbornyl. Cyclopropyl, cyclopentyl and cyclohexyl are particularly preferred.

The aryl substituents may be simple aromatic systems, such as phenyl, biphenyl or terphenyl, or fused systems, such as naphthalenyl, anthracenyl, phenanthrenyl or indenyl, but are preferably phenyl and naphthalenyl.

The hetaryl substituents used may be both simple 5-membered or 6-membered and fused aromatic systems which contain one of the atoms oxygen and sulfur and/or 1 or 2 nitrogen atoms or 1, 2 or 3 nitrogen atoms per ring. Some hetaryl groups which may be advantageously used are mentioned here by way of example: furanyl, thiophenyl, pyrrollyl, oxazolyl, thiazolyl, imidazolyl, isoxazolyl, pyrazolyl, triazolyl, pyridyl, pyrazinyl, pyrimidinyl, pteridinyl, phenanthrolyl, bipyridinyl and quinolrnyl.

The radicals $R^2$ and/or $R^3$ may furthermore carry heterocycloalkyl groups. Groups of this type which may be used are 3-membered or 4-membered heterocycles having one 6-membered to 15-membered monocyclic or fused or bridged tri- or tetracyclic systems with one or, preferably, a plurality of the heteroatoms oxygen, sulfur, nitrogen and/or phosphurus, or 5-membered heterocycles having one or two such systems. Examples of groups of this type are oxiranyl, aziridinyl, tetrahydrofuranyl, pyrrolidinyl, dithianyl, dioxanyl, piperidinyl, piperazinyl and diazabicycloundecanyl.

$R^2$ and $R^3$ may furthermore be interrupted by oxygen, sulfur or $(NR^4)$ groups, where $R^4$ is hydrogen or $C_1$–$C_4$-alkyl, and these heteroatoms or heteroatom groups are each separated by two or more carbon atoms. Preferably used heteroalkylene radicals of this type are heteroalkylene chains composed of ethylene glycol oligomers or non-alkylated or alkylated ethylenediamine oligomers. Of course, the heteroalkyl chains may contain a plurality of different heteroatoms in the chain, but heteroalkyl chains which contain only one heteroatom species are preferred because they are readily available.

If the heteroalkyl chain contains a plurality of $(NR^4)$ groups, the radicals $R^4$ originating from two different $(NR^4)$ groups may form, together with the nitrogen atoms, a 5-membered or 6-membered ring, so that the alkyl or heteroalkyl group is interrupted by imidazolinyl or, preferably, piperazinyl groups.

One or more of the radicals $R^2$ and $R^3$ additionally carry a terminal functional group $F^1$ or $F^2$ which has electron donor properties and is therefore capable of forming a bond, if necessary a coordinate one, with the cations Q. This stabilizes the transition metal complexes, especially when Q is a transition metal cation of oxidation state I or a complex cation of the general formula V or VII.

Preferred functional groups $F^1$ and $F^2$ are alkenyl, alkynyl, $C_5$–$C_{12}$-cycloalkadienyl, nitrile, amino, $C_1$–$C_4$-mono-and dialkylamino, $C_1$–$C_4$-acyl, hydroxyl, $C_1$–$C_4$-alkoxy, aryloxy, $C_1$–$C_4$-alkylsulfido, arylsulfido, $C_1$–$C_4$-dialkyl and diarylphosphido and carboxylato.

The component which is typical and essential for the invention in the novel transition metal complexes of the general formula I and which is responsible for their catalytic and chemical properties, such as stability and solubility, is their component A, which is itself a transition metal complex.

The presence of the complexes A, having the composition described, in the transition metal complexes I leads to a number of advantages. For example, the complexes A are capable, via the oxygen atoms of the phosphonic, phosphinic, arsonic and arsinic ester ligands, of acting as monopodal or, in particular, dipodal or tripodal ligands for other metal ions or cationic metal complexes Q. The complex A thus simultaneously serves as ligand and counterion for other complexes or metal ions Q, which are consequently stabilized by the complex A. This stabilizing effect of the complexes A is particularly important in the complexes I with complexes Q of the general formulae V and VII, which have exceptional chemical stability.

Because of their electron donor properties, the functional groups F present in the complex A furthermore make it possible for metal complex fragments coordinated with the complex A to be stabilized so that these fragments retain their catalytic activity both under the reaction conditions and under the conditions under which the reaction mixture is worked up.

Depending on the composition chosen for the radicals $R^2$ and $R^3$ in complex A, it is furthermore possible to influence the solubility of the transition metal complexes containing this complex. Since these complexes are effective catalysts, the solubility of these catalysts can be tailored to the particular requirements of the reactions to be catalyzed. This permits the use of these homogeneous catalysts in a large number of reactions, for example the hydrogenation of alkenes, alkynes and azomethines and the hydroformylation of alkenes, without the problems described at the outset during removal of the catalyst occurring.

Depending on the type and number of ligands, the complexes A may be neutral (A=complex I) or singly or doubly negatively charged. However, the complexes I in which A is singly negatively charged and bonded to a component Q have particularly advantageous properties. Typical examples of the neutral complexes A are compounds (1) and (2).

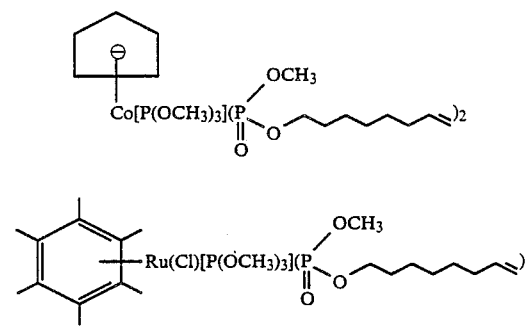

(1)

(2)

Depending on the cation equivalent Q to which the transition metal catalyst A is bonded in the transition metal complexes of the general formula I, the bond between A and Q can be more ionic (salt-like) or coordinate. The boundary between an ionic and a coordinate bond is fluid. Predominantly ionic compounds are the compounds of the general formula I in which A is bonded to protons, alkali metal ions, alkaline earth metal ions or onium ions as cation equivalent Q. Examples of onium ions are ammonium, tetraalkylammonium, arylalkylammonium, alkylpyridinium, tetraarylarsonium, tetraarylphosphonium and tetraalkylphosphonium ions. Since these onium ions only act as a counterion, any such ion may be chosen. This also applies to their substitution pattern.

The transition metal complexes I where $[Q]^+$ is an alkali metal or onium ion, are very suitable for the preparation of the catalytically highly active complexes I in which Q is a complex of the general formula V or VII.

Complexes I in which Q is an alkali metal ion or onium ion are referred to below as complexes A for the sake of simplicity.

Particularly preferred transition metal complexes I are those in which A is selected from the group consisting of the transition metal complexes of the general formula III

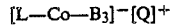 III where E of the group B is phosphorus, the transition metal complexes of the general formula III where E of the group B is phosphorus, c is 0 and $R^3$ is $C_1$–$C_{16}$-alkylene, the transition metal complexes of the general formula IV

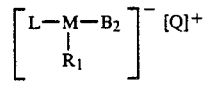 IV where M is selected from the group consisting of rhodium, iridium and ruthenium cations and E of the group B is phosphorus, and the transition metal complexes of the general formula IV where M is selected from the group consisting of rhodium, iridium and ruthenium cations, E of the group B is phosphorus, c is 0 and $R^3$ is $C_1$–$C_{16}$-alkylene.

Examples of such complexes I in which A is bonded to alkali metal ions or onium ions are the compounds (3)–(17).

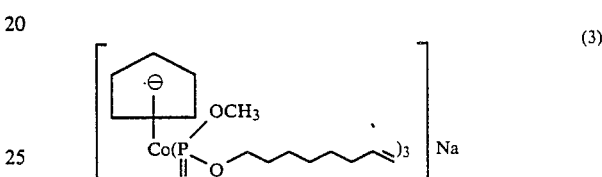

(3)

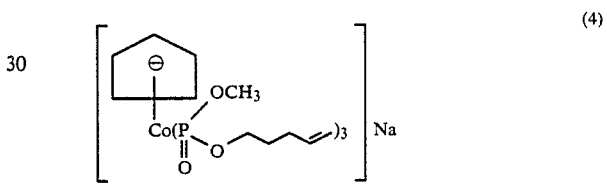

(4)

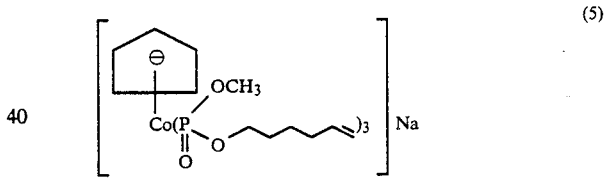

(5)

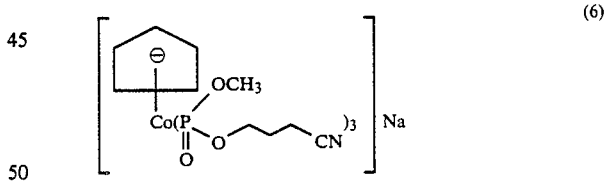

(6)

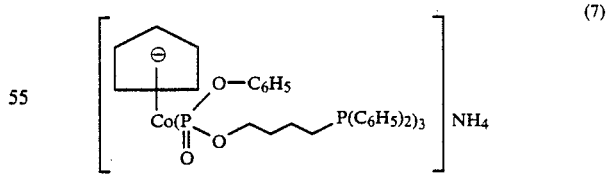

(7)

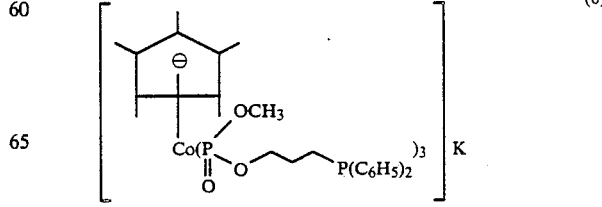

(8)

-continued (9)
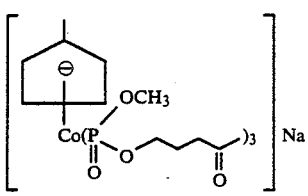

(10)
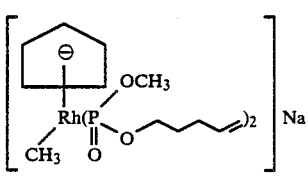

(11)
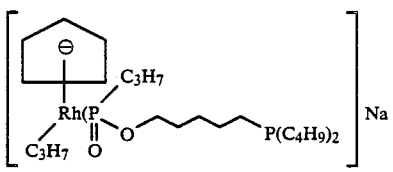

(12)
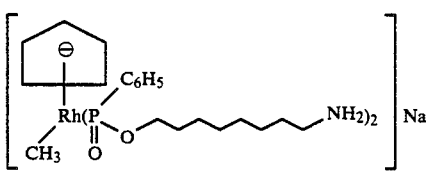

(13)
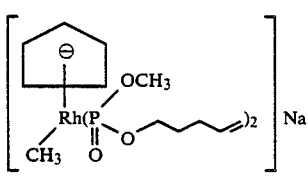

(14)
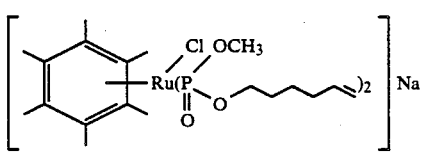

(15)
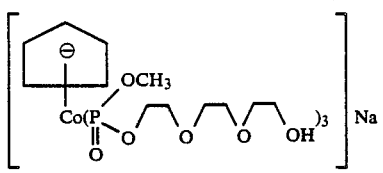

(16)
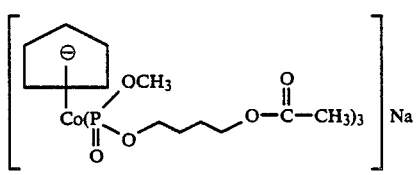

-continued

(17)
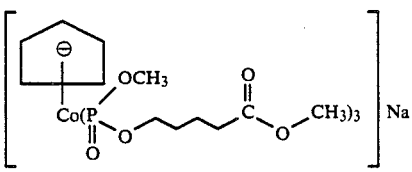

The solubility behavior of these compounds is surprising. For example, the compounds (3), (4), (10) and (14) are very readily soluble in hydrocarbons but insoluble in water; on the other hand, for example, the compounds (9) and (15) are very readily soluble in water.

Complexes which contain ligands having a structure similar to that of A, i.e. having methyl phosphonates and ethyl phosphonates as ligands of the central ion M but without functional groups $F^1$ and $F^2$, have been described in the literature and are known for their strong complexing power with respect to transition metal cations. These known complexes have exceptional stability but are not very suitable for catalytic purposes (cf.: W. Kläui et al., Angew. Chem. 97 (1985), 697; W. Kläui et al., Chem. Ber. 115 (1982), 1922; W. Kläui et al., J. Organometal Chem. 331 (1987), 317; W. Kläui, Z. Naturforsch. 34B (1979), 1403).

The chemical and thermal stability of complexes A, in particular that of the cobalt complexes, is particularly noteworthy. These are stable up to 250° C., are not oxidized in solution or in the solid state by atmospheric oxygen and do not decompose even in concentrated acids, such as hydrochloric acid, provided that the functional groups F do not react under these conditions.

Another advantage is that the complexes I are readily available. In general, they are synthesized by first preparing the complexes A. For the preparation of the complexes A having cobalt as the central ion, cobalt carbonyl complexes, such as [LCo(CO)$_2$] or [LCo(CO)I$_2$], in which L has the abovementioned meanings, are advantageously used as starting materials.

In simple ligand exchange reactions with tertiary phosphites, the corresponding cobalt phosphite complexes can be prepared from these (cf. Schleman et al., J. Organometal. Chem. 323 (1987), 103; W. Kläui et al., Chem. Ber. 115 (1982), 1922). These phosphite complexes are converted in the presence of halide ions, preferably iodide ions, alkyl halides, preferably alkyl iodides, or pseudohalide ions, preferably cyanide ions, in a Michaelis-Arbuzov reaction, into the corresponding phosphonic ester complexes. Depending on the reaction conditions used (amount of reagents, reaction temperature), it is possible to control both the extent of ligand exchange and the extent of phosphite/phosphonic acid conversion in these reactions, so that finally complexes having 1, 2 or 3 phosphonic ester ligands and 2, 1 or 0, respectively, ligands $R^1$ can be obtained.

For the preparation of the complexes I in which A is a rhodium(I) complex, rhodium(I)-olefin compounds, such as cyclooctadiene(COD)rhodium(I) chloride [(COD)RhCl]$_2$, are preferably used as starting materials. These can be converted by ligand exchange with tertiary phosphites into the corresponding rhodium(I) phosphite complexes according to equation (a), where the groups R may be identical or different and correspond in their composition to the composition stated for the groups $R^2$ and $R^3$.

((COD)RhCl)$_2$ + 4P(OR)$_3$ → 2Rh(Cl)[P(OR)$_3$]$_2$  (a)

The desired ligand L can then be introduced into the complex by exchanging the chloride ligand with, for example, cyclopentadienylthallium. The phosphite complex thus obtained can then be converted into the phosphonate complex A, once again via a Michaelis-Arbuzov reaction (cf.: H. Werner et al., Z. Anorg. Allg. Chem. 458 (1979), 301).

The complexes I in which A contains iridium or ruthenium as the central ion M are synthesized in a similar manner.

The preparation of the metal complexes used as starting materials is known and is described in the cited publications or textbooks such as Brauer, Handbuch der Präparativen Anorganischen Chemie, Enke, 3rd Edition, Volume 3, Stuttgart, 1981.

Tertiary phosphites which are esterified with identical or different alcohols are obtained by the methods described in Houben-Weyl, Methoden der Organischen Chemie, Volume XII/2, pages 53–73, Thieme, Stuttgart 1964.

Complexes I in which A contains phosphinate ligands are prepared in the same manner, i.e. by ligand exchange reactions with phosphinite esters followed by a Michaelis-Arbuzov reaction. The phosphinite esters used are prepared by methods described in the literature (cf.: Houben-Weyl, Methoden der Organischen Chemie, Volume XII/1, pages 247–261, Thieme, Stuttgart, 1964).

The same applies to the preparation of the complexes I in which A contains arsonate or arsinate ligands.

Depending on whether they contain two or three phosphonate and/or phosphinate or arsonate and/or arsinate groups, the novel complexes A behave like bidentate or tridentate oxygen ligands. As tridentate oxygen ligands, the complexes A are six-electron donors and are formally isoelectronic with the cyclopentadienyl ligands and, like these, are capable of forming complexes with virtually all transition metal ions, which may be in a very wide range of oxidation states. It is noteworthy that the complexes A, as tridentate oxygen ligands, can form complexes I with organometallic complex fragments of low valency, the said complexes I frequently being more stable than the corresponding complexes with the cyclopentadienyl ligands.

In the case of the bidentate or monodentate oxygen ligands A, the functional groups $F^1$ and $F^2$ of groups $R^2$ and/or $R^3$ assume the role of electron donor and thus help to stabilize the complexes I of A with organometallic complex fragments Q of the general formulae V and VII.

Transition metal complexes I in which $[Q]^+$ is a complex cation of type V $$[M^Q Z]^{x\oplus} \quad \quad V$$

where X is 0, 1 or 2, $M^Q$ is rhodium, iridium, ruthenium, chromium, tungsten, molybdenum, manganese, rhenium or copper, Z is one of the bidentate ligands cycloheptatriene, $C_5$–$C_{12}$-cycloalkadiene, $C_4$–$C_8$-alkadiene or a $C_2$–$C_6$-alkylenediphosphido ligand of the general formula VI $$R^6\text{—}P\text{—}(CH_2)_{1-6}P\text{—}R^6 \quad \quad VI$$

where $R^6$ is $C_1$–$C_4$-alkyl and/or phenyl, and/or from 1 to 3 identical or different ligands from the group consisting of the monodentate ligands carbonyl, nitrosyl, chlorine, bromine, iodine, nitrile, isonitrile, $C_1$–$C_4$-alkyl, $C_1$–$C_4$-acyl, $C_1$–$C_4$-alkene, $C_1$–$C_4$-alkyne, $C_1$–$C_4$-trialkylphosphino, triarylphosphino and/or carbyne ligands, and of course with the proviso that the number of ligands Z is dependent on the coordination number of the metals $M^Q$, are advantageously prepared from transition metal complexes I in which Q is an alkali metal ion or onium ion.

At this point, some synthesis routes for the preparation of the complexes I, where Q is a complex of the general formula V, are described by way of example.

Particularly suitable starting materials for the preparation of the complexes I in which $M^Q$ is tungsten, chromium or molybdenum have proven to be the carbonyl complexes of these metals. These can be subjected to simple ligand exchange with the ligand A to give the corresponding complexes I with Q of the general formula V.

For example, the compound hapto-7-cycloheptatrienyl-tricarbonyl-tungsten $[(h^7—C_7H_7)W(CO)_3]^+$ can be reacted with salts of the complexes $[A]^-$ to give compounds of type $([A][W(CO)_2(h^3—C_7H_7)])$. The reaction of the complexes A with carbyne complexes, such as trans[$BrMo(CO)_4$(phenylcarbyne)], to give complexes VII of type $[A][Mo(CO)_2$(phenylcarbyne)$]$ is similar. Of course, this reaction can also be carried out with carbyne ligands other than phenylcarbyne.

The anionic complexes which can be prepared from the carbonyl complexes of tungsten, chromium and molybdenum of the formal oxidation state 0 by ligand exchange with the transition metal complexes A can likewise advantageously be used for the preparation of the complexes I with Q of the general formula V. For example, anionic complexes of type $([A][M^Q(CO)_3])^-$ are obtained by reacting the triacetonitrile-tricarbonyl complexes $[(CH_3CN)_3M^Q(CO_3]$ of tungsten, of chromium and of molybdenum with the complexes A. If the solutions of these compounds are acidified with dilute mineral acids or organic acids, the conjugated acids $([A][M^Q(CO)_3])$–$H^+$ are obtained. These are converted into the corresponding novel hapto-3-dimethylallyl complexes $[A][M^Q(CO)_3(h^3$-dimethylallyl$)]$ in the presence of isoprene.

In most cases, however, the detour via the conjugated acid is not necessary. For example, the reaction of the tricarbonyl complexes $([A][M^Q(CO)_3])^-$ of tungsten, of chromium and of molybdenum with N-methyl-N-nitroso-4-toluenesulfonamide gives the corresponding novel nitrosyl complexes $[A][M^Q(CO)_3(NO)]$.

The anionic tricarbonyl complexes of tungsten, of chromium and of molybdenum can also be converted into the novel complexes I, where Q is of the general formula V, by chemical reactions in the ligand sphere. Thus, in the reaction of the salts of the tricarbonyl complexes $([A][M^Q(CO)_3])^-$ of tungsten, of chromium and of molybdenum with $C_1$–$C_4$-alkyl iodides RI, simple addition of an alkyl radical at the carbonyl complex takes place on the one hand, giving the complexes I of type $[A][M^Q(CO)_3R]$, while at the same time this reaction also gives dicarbonylhapto-2-acyl complexes I $[A][MQ(CO)_2(h^2—COR)]$, in which a carbonyl ligand has reacted with the alkyl radical with formation of an acyl ligand. These two reaction products can readily be separated from one another by column chromatography.

A similar chemical transformation in the ligand sphere takes place in the oxidation of the complexes I $[A][M^Q(CO)_3(CH_3)]$ in an oxygen atmosphere. The corresponding dioxo-acetato complex I [A][M$^Q$(O)$_2$-(acetate)] is formed.

A similar procedure is adopted for the preparation of the complexes I in which Q of the general formula V is a manganese or rhenium complex. Thus, the reaction of complexes A with halo-pentacarbonyl complexes, such as [BrM$^Q$(CO)$_5$], of manganese and of rhenium gives the novel complexes I [A][M$^Q$(CO)$_3$] by ligand exchange.

For the preparation of the complexes I where M$^Q$ is rhodium, iridium or ruthenium, the halides of these metals are generally used as starting materials. Thus, the reaction of the complexes A with ruthenium trichloride under a carbon monoxide atmosphere leads to complexes I of type [A][Ru(CO)$_2$Cl]. The corresponding rhodium and iridium complexes can be obtained in the same way. Further complexes I can be prepared from these compounds by ligand exchange. For example, the reaction of [A][Ru(CO)$_2$Cl] with triphenylphosphine (PPh$_3$) gives a mixture consisting of [A][Ru(PPh$_3$)-(CO)Cl] and ([A][Ru(PPh$_3$)(CO)$_2$Cl], from which the individual compounds can be isolated by column chromatography.

Of course, the complexes I of rhodium, of ruthenium and of iridium can also be obtained by reacting the complexes A with complexes of these metals. Thus, the complexes I of type [A][Ir(COD)] and [A]-[Ir(CH$_2$=CH$_2$)$_2$] are obtained, for example, from the dinuclear iridium-cyclooctadiene(COD)-dichloro complex [Ir(COD)Cl]$_2$ and from the dinuclear iridium-diethyleno-chloro complex [Ir(CH$_2$=CH$_2$)$_2$-Cl]$_2$, respectively, and the reaction of the dinuclear rhodium complex [Rh(CO)$_2$Cl]$_2$ with the complex A leads to the dicarbonyl complexes I [A][Rh(CO)$_2$]. These in turn are in equilibrium with the monocarbonyl complexes I [A][Rh(CO)], depending on the temperature and the carbon monoxide partial pressure over the compound or its solutions. All these complexes I can be prepared with iridium, ruthenium or rhodium as the central atom M$^Q$. If it is intended to obtain the monocarbonyl complexes selectively, the elimination of carbon monoxide is advantageously carried out photochemically by exposing the dicarbonyl complexes to UV light.

For the synthesis of the complexes I with copper as the central atom M$^Q$, copper(II) complexes ([A]$_2$Cu) are preferably used as starting materials, the said copper complexes being readily obtainable by reacting copper-(II) salt solutions with solutions of complexes A. These are reduced to copper(I) monocarbonyl complexes I [A][Cu(CO)] in the presence of finely divided metallic copper under a carbon monoxide atmosphere. However, these can also be prepared starting from tetraacetonitrilocopper(I) complexes [Cu(CH$_3$CN)$_4$]$^+$ or other solvate complexes of copper by ligand exchange with the complexes A under a carbon monoxide atmosphere. If this reaction is carried out in the presence of alkenes or alkynes instead of carbon monoxide, the alkene- or alkyne-copper complexes I [A][Cu(alkene)] or [A][Cu(alkyne)] are obtained. If bifunctional alkenes, such as butadiene or cyclooctadiene, are used in this reaction, this leads to the formation of the dinuclear complexes (18) and (19)

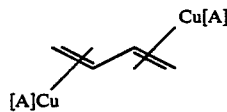 (18)

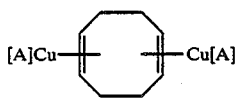 (19)

where the copper-alkene complex corresponds to one cation equivalent Q of the general formula VII.

For the preparation of the complexes I where Q is of the general formula VII and M$^Q$ is rhodium, iridium or ruthenium, dicarbonyl complexes I of type [A][M$^Q$-(CO)$_2$] are advantageously used as starting materials. The said dicarbonyl complexes dimerize at elevated temperatures with elimination of carbon monoxide to form complexes I, such as [A][Rh—$\mu$(CO)$_3$—Rh][A]. The Greek letter $\mu$ in the formula is intended to indicate that the carbonyl ligands are bridging ligands.

If complexes I having different central atoms M$^Q$ rhodium, iridium and ruthenium are present in the reaction mixture, bridged dinuclear complexes having two central atoms M$^Q$ per complex Q also form under these conditions In the presence of a high carbon monoxide partial pressure, the dimeric complexes can be converted back into the monomeric complexes [A][M-(CO)$_2$].

Complexes I in which the complex Q of the general formula VII contains various bridging ligands per complex molecule can be obtained both from the complexes I of type [A][M$^Q$(CO)$_2$] and from complexes which are prepared therefrom and in which Q is of the general formula VII, in the presence of alkadienes, cycloalkadienes, alkyl isonitriles and/or phosphido compounds by a ligand exchange reaction.

The complexes I in which Q is a transition metal ion or, in particular, a transition metal complex of the general formula V or VII have noteworthy catalytic properties. The complexes I in which Q is an alkali metal ion or onium ion likewise have catalytic activity but this is inferior to the catalytic activity of the abovementioned complexes I.

Complexes I in which Q of the general formula V is a dication are obtained, for example, by reacting a complex A with a dicationic metal complex [Ru(hexamethylbenzene)Cl$_2$] or [Rh(pentamethylcyclopentadienyl)Cl$_2$]. This gives the complexes I of the formulae [A][Ru(hexamethylbenzene]$^+$ and [A][Rh(pentamethylcyclopentadienyl]$^+$, respectively.

Furthermore, in the transition metal complexes as claimed in claim 1, in which [Q]$^+$ is a complex dication of the general formula VII $$[M^Q-K-M^Q]^{2+} \qquad \text{VII}$$

where the ligands K are from 1 to 3 of the bridging ligands from the group consisting of carbonyl, C$_4$-C$_6$-alkadienyl, C$_8$-C$_{12}$-cycloalkadiene, C$_1$-C$_4$-alkylisonitrile, C$_1$-C$_4$-dialkylphosphido, diarylphosphido and/or C$_1$-C$_6$-alkylenediphosphido ligands of the general formula VI and whose preparation has been described above, the number of bridging ligands K does of course depend on the coordination number of the particular metals M$^Q$ in the complex Q and on the number of coordination sites of the particular complex ligands A. The number of bridging ligands K cannot be larger because the number of coordination sites in the complex I, defined as the sum of the coordination sites of the complex ligands A, without taking into account their functional groups F, and of the coordination sites of the ligands K, does not exceed the sum of the coordination numbers of the particular metals $M^Q$ in the complex VII.

The complexes I with Q of the general formulae V and VII are preferably used as catalysts for the cyclotrimerization of acetylene compounds, for the catalytic hydrogenation of unsaturated compounds, such as alkenes, alkynes, aldehydes or azomethines, and for the hydroformylation of $C_2$-$C_{10}$-alkenes.

It may be advantageous to use mixtures of these compounds with one another or mixtures of these compounds with other catalysts, promoters and/or cocatalysts. If complexes with Q of the general formulae V and VII are used as catalysts, it often proves advantageous to prepare these compounds in situ in the reaction solution.

In the spectroscopic investigation of such reaction solutions, it is frequently observed that a plurality of the complexes described, in particular the carbonyl complexes Q of the general formulae V and VII, are present side by side in equilibrium in the hydroformylation reaction.

A certain complex may be preferentially formed, depending in particular on the carbon monoxide partial pressure. In such systems, the carbon monoxide should therefore be regarded not only as a reactant but also as a promoter.

By using cocatalysts, for example triphenylphosphine, it is possible to control the selectivity of the reaction. Since the n/iso ratio in the hydroformylation also depends on the particular catalyst used, the use of the individual catalytically active, novel complexes, mixtures of these complexes or their mixtures with promoters or cocatalysts constitutes a further possible method for controlling the selectivity.

Regarding the reactants in solution, the novel catalysts are generally used in molar ratio of from 1:50 to 1:10,000, preferably from 1:100 to 1:1,000, particularly preferably from 1:100 to 1:800.

Molar ratios of from 1:100 to 1:200 are preferred in the cyclotrimerization of acetylene compounds, while molar ratios of from 1:500 to 1:1,000 are preferred in the hydrogenation of unsaturated compounds and in the hydroformylation of alkenes.

The cyclotrimerization of acetylene compounds is carried out using the novel catalysts in general at from 80° to 150° C. under atmospheric or superatmospheric pressure. The cyclotrimerization is preferably effected under atmospheric pressure and at from 100° to 120° C.

The alkenes and alkynes can be hydrogenated using the novel catalysts at room temperature or at up to 200° C. However, temperatures of from 50° to 100° C. are preferred. The hydrogenation is usually carried out under a hydrogen pressure of from 10 to 100 bar. If necessary, lower or higher pressures may also be used. Thus, where mild reaction conditions are used, it is possible to hydrogenate alkynes only as far as the alkene stage. If it is intended to hydrogenate carbonyl compounds, hydrogen pressures of up to 300 bar may be necessary, depending on the catalyst used and on the carbonyl compound to be hydrogenated. The Examples which follow illustrate the invention.

EXAMPLE 1

Preparation of the compounds
$Na[(C_5H_5)Co[P(O)(OCH_3)(O-R^3-F^2)]]$

General method

One equivalent of the cobalt compound $[(C_5H_5)Co-(CO)I_2]$ was slowly added to a solution of 3 equivalents of the phosphorous triester $P(OCH_3)_2(OR^3-F)$ in acetone.

The initially black-violet solution rapidly became yellowish brown with evolution of carbon monoxide. It was stirred for 12 hours at room temperature, one equivalent of sodium iodide was then added and stirring was continued for a further 12 hours. The solvent was distilled off and the residue was chromatographed over a column of silica gel of activity III. The byproducts formed were first removed using an eluent mixture consisting of 2:1 (v/v) dichloromethane/acetone. The product was then eluted from the column using an eluent mixture consisting of 1:2 (v/v) acetone/methanol. The solvent was distilled off and the product was obtained in pure form.

1.1 $Na[(C_5H_5)Co([P(O)(OCH_3)(O-CH_2-CH_2-CH_2-CH=CH_2)]_3]$

Preparation as described in the general method. Mixture: 4646 g (26.08 mmol) of $P(OCH_3)_2(OCH_2-CH_2-CH_2-CH=CH_2)$
3.5 g (8.62 mmol) of $[(C_5H_5)Co(CO)I_2]$
1.29 g (8.61 mmol) of NaI
in 50 ml of acetone.

Yield: 4.1 g (76%)

$^1H$—NMR (80 MHz, $CDCl_3$); $\delta=1.51-1.84$("p") comprising t/t, $^3J_{HCCH}=6.5$ Hz, 6H, 3 $POCH_2CH_2CH_2CH=CH_2$), 2.03-2.29("q") comprising d/t, $^3J_{HCCH}=6.6$ Hz, 6H, 3 $POCH_2CH_2CH_2CH=CH_2$), 3.58(virt.q, $^3J_{POCH}=10.4$ Hz, 9H, 3 $POCH_3$), 3.92(sym.m, 6H, 3 $POCH_2CH_2$—), 4.95(d/m, $^3J_{HC=CH(cis)}=9.9$ Hz, 3H, 3—HC=CHH$_{cis}$), 5.0(s, 5H, $C_5H_5$), 4.98(d/m, $^3J_{HC=CH(trans)}=17.4$ Hz, 3H, 3HC=CHH$_{trans}$), 5.82(t/d/d, $^3J_{HCCH}=6.3$ Hz, $^3J_{HC=CH(cis)}=9.9$ Hz, $^3J_{HC=CH(trans)}=17.4$ Hz, 3H, 3—$CH_2CH=CH_2$) $^{31}P\{^1H\}$—NMR (32 Mhz, $CDCl_3$ at $-60°$ C.); $\delta=106.8(s)$ IR (film on KBr, $cm^{-1}$); $V(C=C)$ 1640 m, $V(P=O)$ 1160 ss, $\delta(C=C-H$ of $C_5H_5)$ 830 s, $\delta(P=O)$ 580 s 1.2 $Na[(C_5H_5)Co(P(O)(OCH_3)(O-(CH_2)_6-CH=CH_2)]_3]$ Preparation as described in the general method.
Mixture:
8.70 g (39.5 mmol) of $P(OCH_3)_2(O-(CH_2)_6-CH=CH_2)$
5.30 g (13.06 mmol) of $[(C_5H_5)Co(CO)I_2]$
1.95 g (13.01 mmol) of NaI
in 50 ml of acetone Yield: 7.07 g (71%)

$^1H$—NMR (80 MHz, $CDCl_3$); $\delta=1.37-1.85$ (m, 24H, 3 $OCH_2CH_2CH_2CH_2CH_2CH_2CH=CH_2$), 1.94-2.09 (m, 6H 3 $CH_2CH_2CH=CH_2$), 3.59(virt.q, $^3J_{POCH}=10.4$ Hz, 9H, 3 $POCH3$), 3.89(sym.m, 6H$_4$, 3 $POCH_2CH_2$—), 4.94 (d/m), $^3J_{HC-CH(cis)}=9.9$ Hz, 3H, 3—HC=CHH$_{cis}$), 4.98(d/m, $^3J_{HC}$ $_{-CH(cis)}=9.9$ Hz, 3H, 3—HC=CHH$_{cis}$), 4.98(d/m, $^3J_{HC=CH(trans)}=17.3$ Hz, 3H, 3—CH=CHH$_{trans}$), 5.01(s, 5H, $C_5H_5$), 5.86(t/d/d, $^3J_{HCCH}=6.5$ Hz, $^3J_{HC=CH(cis)}=9.9$ Hz, $^3J_{HC=CH(trans)}=17.3$ Hz, 3H, 3—$CH_2CH=CH_2$) $^{31}P[^1H]$—NMR (32 MHz, $CDCl_3$ at $-60°$ C.): $\delta=10.69(s)$ IR (film on KBr, cm$^{-1}$): $\nu$(C≡C) 1640 m, (P=O) 1160 ss, $\delta$(C=C—H of C$_5$H$_5$) 830 m, $\delta$(P=O) 580 s.

1.3  Na[(C$_5$H$_5$)Co[P(O)(OCH$_3$)(O—CH$_2$—CH$_2$—CH$_2$—CN)]$_3$]

Preparation as described in the general method.
Mixture:
1.859 g (10.5 mmol) of P(OCH$_3$)$_2$(O—(CH$_2$—CH$_2$—CH$_2$)—CN)
1.209 g (2.96 mmol) of [(C$_5$H$_5$)Co(CO)I$_2$]
0.60 g (4.0 mmol) of NaI
in 40 ml of acetone
Yield: 1.84 g (98%)

$^1$H—NMR (80MHz, CDCl$_3$); $\delta$ = 1.96("p" comprising t/t, $^3J_{HCCH}$ = 6.5 Hz, 6H, 3 OCH$_2$CH$_2$CH$_2$CN), 2.58 (t, $^3J_{HCCH}$ = 6.8 Hz, 6H, 3 CH$_2$CH$_2$CH$_2$CN), 3.60(virt.q, $^3J_{POCH}$ = 10.5 Hz, 9H, 3 POCH3), 3.7–4.2-(sym.m, 6H), 3 POCHCH$_2$—), 5.06(s, 5H, C$_5$H$_5$) $^{31}$P[H]—NMR (32 MHz, CDCl$_3$ at −60° C.): $\delta$ = 107.8(s) IR (film on KBr, cm$^{-1}$): $\nu$(C≡N) 2445 m, $\nu$(P=O) 1160-1135 ss, $\nu$(P—O) 1040-1005 vs, $\delta$(C=C—H of C$_5$H$_5$) 830 m, $\delta$(P=O) 570 s 1.4 Na [(C$_5$H$_5$)Co[P(O)(OCH$_3$)(O—(CH$_2$)$_6$—CN)]$_3$)

Preparation as described in the general method.
Mixture:
6.824 g (31.13 mmol) of P(OCH$_3$)$_2$(O—(CH$_2$)$_6$—CN)
3.90 g (9.61 mmol) of [(C$_5$H$_5$)Co(CO)I$_2$]
1.555 g (10.38 mmol) of NaI
in 100 ml of acetone
Yield: 7.0 g (96%)

$^1$H—NMR (80 MHz, CDCl$_3$); $\delta$ = 1.0–2.0(m, 24H, 3 CH$_2$CH$_2$CH$_2$CH$_2$CH$_2$CH$_2$CN), 2.36(t, $^3J_{HCCH}$ = 6.3 Hz, 6H, 3 —CH$_2$CH$_2$CN), 3.57(virt.q, $^3J_{POCH}$ = 9.9 Hz, 9H, 3 POCH3), 3.67-4.0(sym.m, 6H, 3 POCH$_2$CH$_2$—), 5.01(s, 5H, C$_5$H$_5$) $^{31}$P[$^1$H]—NMR (32 MHz, CDCl$_3$ at −60° C.): $\delta$ = 108.4(s) IR (film on KBr, cm$^{-1}$): $\nu$(C≡N) 2245 w, $\nu$(P=O) 1160 vs, $\nu$(P—O) 1050-1010 vs, $\delta$(C=C—H of C$_5$H$_5$) 830 m, $\delta$(P=O) 570 s.

1.5 Na[(C$_5$H$_5$)Co{P(O)(OCH$_3$)(O—CH$_2$—CH$_2$—CH$_2$—C(O)—CH$_3$)}$_3$]

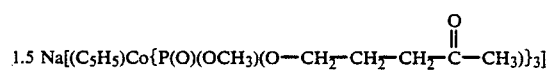

Preparation as described in the general method.
Mixture:
3.24 g (16.61 mmol of

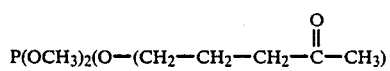

P(OCH$_3$)$_2$(O—(CH$_2$—CH$_2$—CH$_2$—C(O)—CH$_3$)

2.247 g (5.53 mmol) of [(C$_5$H$_5$)Co(CO)I$_2$]
0.83 g (5.53 mmol) of NaI
Yield: 2.92 g (77%)

$^1$H—NMR (80 MHz, CDCl$_3$); 1.86("p", $^3J_{JCCH}$ = 6.7 Hz, 6H, 3 CH$_2$CH$_2$CH$_2$C(O)(CH$_3$), 2.17(s, 9H, 3 CH$_2$C(O)CH$_3$), 2.57(t, $^3J_{HCCH}$ = 7.1 Hz, 6H, 3 CH$_2$CH$_2$C(O)CH$_3$), 3.56virt.q, $^3J_{POCH}$ = 9.8 Hz, 9H, 3 POCH3), 3.90(sym.m comprising t/virt.q, 6H, 3POCH$_2$CH$_2$), 5.00(q, $^3J_{POCH}$ = 0.3 Hz, 5H, C$_5$H$_5$) $^{31}$P[$^1$H]—NMR (32 MHz, CDCl$_3$ at −60° C.): $\delta$ = 107.1(s) IR (film on KBr, cm$^{-1}$): $\nu$(C=O) 1712 vs, $\nu$(P=O) 1165 ss, 1140 s, $\nu$(P—O) 1050-1000 vs, $\delta$(C=C—H of C$_5$H$_5$) 830 m, $\delta$(P=O) 570 s

EXAMPLE 2

Preparation of the compounds Na[(C$_5$H$_5$)Rh(CH$_3$)[P(O)(OCH$_3$) O—R$^3$—F$^3$)]$_2$]

General Method

The phosphorous triester P(OCH$_3$)$_2$(O—R$^3$—F) was slowly added to a stirred solution of cyclooctadienerhodium chloride [[(COD)RhCl]$_2$] in 40 ml of dichloromethane at room temperature. During this procedure, the color of the solution became paler, changing from orange to pale yellow. Stirring was carried out for 2 hours. Thereafter, all volatile components of the reaction mixture were stripped off under greatly reduced pressure. The residue was taken up in 30 ml of tetrahydrofuran, and a slight excess of cyclopentadienylthallium Tl(C$_5$H$_5$) was added to this solution. The resulting suspension was stirred for 24 hours at room temperature. The solvent was then distilled off under reduced pressure. The red residue was chromatographed with diethyl ether over a column of silica gel of activity level III. The first yellow fraction which was eluted was collected and evaporated down. It contained the rhodium compound [(C$_5$H$_5$)Rh[P(OCH$_3$)$_2$(O—R$^3$—F)]$_2$]. This compound was dissolved in 50 ml of acetone. Sodium iodide was added to this solution, which was then heated at 50° C. for from 6 to 8 hours. The course of the reaction was monitored by NMR spectroscopy. After the reaction had ended, the solvent was removed and the product was extracted with toluene to remove excess sodium iodide. The extracting agent was distilled off and the pure product was obtained.

2.1 Na[(C$_5$H$_5$)Rh(CH$_3$)[P(O)(OCH$_3$)(O—CH$_2$—CH$_2$—CH=CH$_2$)]$_2$]

Preparation as described in the general method.
Mixture:
1.242 g (6.97 mmol) of P(OCH$_3$)$_2$(O—CH$_2$CH$_2$CH$_2$CH=CH$_2$)
0.8 g (1.62 mmol) of [[(COD)RhCl]$_2$]
1.1 g (4.08 mmol) of Tl(C$_5$H$_5$)
1.05 g (7.0 mmol) of NaI
Yield: 1.48 g (86%)

$^1$H—NMR (80 MHz, CDCl$_3$); 0.63 (m, 3H, RhCH$_3$), 1.10–2.00(m, 4H, 2 OCH$_2$CH$_2$CH$_2$CH=CH$_2$), 1.98-2.18("q", $^3J_{HCCH}$ = 6.3 Hz, 4H, 2 OCH$_2$CH$_2$CH$_2$CH=CH$_2$), 3.52(virt.t, $^3J_{POCH}$ = 11.9 Hz, 6H, 2 POCH3), 3.86(sym.m, 4H, 2 POCH$_2$CH$_2$—), 4.95(d/m), $^3J_{HC-CH}$ = 9.9 Hz, 2H, 2 —CH=CHH$_{cis}$), 4.98(d/m, $^3J_{HC-CH(trans)}$ = 17.4 Hz, 2H, 2 —CH=CHH$_{trans}$), 5.32(t, $^3J_{PRhCH}$ = 2.2 Hz, 5H, C$_5$H$_5$), 5.82(t/d/d, $^3J_{HCCH}$ = 6.4 Hz, $^3J_{HC=CH(cis)}$ = 9.9 Hz, $^3J_{HC=CH(trans)}$ = 17.4 Hz, 2H, 2 —CH$_2$CH=CH$_2$) $^{31}$P[$^1$H]—NMR (CDCl$_3$ at −60° C.): $\delta$ = 102.6(d, $^1J_{RhP}$ = 209 Hz)

IR (film on KBr, cm$^{-1}$): $\nu$(C=C) 1640 m, $\nu$(P=O) 1130 vs, $\delta$(P=O) 570 s 2.2 Na[(C$_5$H$_5$)Rh(CH$_3$)[P(O)(OCH$_3$(O—CH$_2$—CH$_2$—CH$_2$—CN)]$_2$]

Preparation as described in the general method.
Mixture:
2.11 g (11.9 mmol) of P(OCH$_3$)$_2$(O—CH$_2$CH$_2$—CH$_2$—CN)
1.145 g (2.32 mmol) of [[(COD)RhCl]$_2$]
1.785 g (6.52 mmol) of Tl(C$_5$H$_5$)
1.66 g (11.1 mmol) of NaI
Yield: 1.48 g (70%)

$^1$H—NMR (80 MHz, CDCl$_3$); $\delta$32 0.64(m, 3H, RhCH$_3$), 1.98("p" comprising t/t, $^3J_{HCCH}$ = 6.1 Hz, 4H, 2 POCH$_2$CH$_2$CH$_2$CN),2.54(t,$^3J_{HCCH}$=6.6 Hz, 4H, 2 POCH$_2$CH$_2$CH$_2$CN), 3.54virt.t, $^3J_{POCH}$=12.1 Hz, 6H, 2 POCH3), 3.83-4.12(m, 4H, 2 POCH$_2$CH$_2$—), 5.39(t, $^3J_{PRhCH}$=2.3 Hz, 5H, C$_5$H$_5$) $^{31}$P[$^1$H]—NMR (32 MHz, CDCl$_3$ at −60° C.): δ=110.1(d, $^1J_{RhP}$=210.6 Hz)

IR (film on KBr, cm$^{-1}$): ν(C≡N) 2250 m, ν(P=O) 1119 vs, ν(P=O) 1035-1020 vs, δ(P=O) 585 s.

EXAMPLE 3

Preparation of the compounds
[A]Rh(μ—CO)$_3$Rh[A]:(A:[(C$_5$H$_5$)Co[P(O)(OCH$_3$)(O—R$^3$—F$^2$)]$_3$]$^-$)

General Method 2 equivalents of the complex salt Na$^+$[A]$^-$ were added to a solution of one equivalent of rhodium compound [[CO)$_2$RhCl]$_2$] in dichloromethane, and the mixture was stirred. The course of the reaction was monitored by IR spectroscopy. After 30 minutes, the complex ([A][Rh(CO)$_2$]) had formed from the starting compounds. The solution was then refluxed until no further carbon monoxide formed. Decarbonylation gave the complex [A]Rh(μ—CO)$_3$Rh[A]. During the reaction, observation of the IR spectrum of the mixture showed that the intensity of the bands at 2080 and 2000 cm$^{-1}$, which were assigned to the compounds ([A][Rh(CO)$_2$]), decreased and a new band was formed at 1840 cm$^{-1}$, which was assigned to the compounds [A]Rh-(μ—CO)$_3$Rh[A]. After the end of the reaction, the reaction mixture was cooled, the solvent was distilled off and the product was extracted from the residue with hexane.

3.1 [A]Rh(μ—CO)$_3$Rh[A]; [A]:[(C$_5$H$_5$)Co[P(O)(OCH$_3$)(O—(CH$_2$)$_6$—CH=CH$_2$)]$_3$]

Preparation as described in the general method.
Mixture:
0.785 g (1.029 mmol) of Na[A]
0.2 g (0.514 mmol) of [[(CO)$_2$RhCl]$_2$]
in 50 ml of dichloromethane
Yield: 0.72 g (79%)
$^1$H—NMR (80 MHz, CDCl$_3$); δ=3.66(virt.q, $^3J_{POCH}$=10.5 Hz, 18H, 6 POCH3), 3.97(sym.m, 12H, 6 POCH$_2$CH$_2$—), 4.98(s, 10H, 2 C$_5$H$_5$). The resonance signals of the other protons remained unchanged in comparison with the starting compound Na[A] from Example 1.2.
IR (film on KBr, cm$^{-1}$): ν(CO) 1840 vs, ν(C=C) 1640 w, ν(P=O) 1110 vs, δ(C=CH—H of C$_5$H$_5$) 830 m, δ(P=O) 590 s. 3.2 [A]Rh(μ—CO)$_3$Rh[A]; [A]:[(C$_5$H$_5$)Co[P(O)(OCH$_3$)(O—(CH$_2$)$_6$CN)]$_3$]$^-$ Preparation as described in the general method.
Mixture:
0.16 g (0.21 mmol) of Na[A]
0.04 g (0.103 mmol) of [[(CO)$_2$RhCl]$_2$]
in 20 ml of dichloromethane
Yield: 0.115 g (63%)
IR (film on KBr, cm$^{-1}$): ν(C≡N) 2245 w, ν(CO) 1835 vs, ν(P=O) 1110 vs, ν(P—O) 1040-1000 vs, δ(C=C—H of C$_5$H$_5$) 830 m, δ(P=O) 590 s.

EXAMPLE 4

Preparation process for the compounds [A]Rh(CO); [A]:[(C$_5$H$_5$)Co[P(O)(OCH$_3$)(O—R$^3$—F)]$_3$]

Method (a)

(a) A solution of the compound [A]Rh(μ—CO)$_3$Rh[A] in toluene was refluxed for 4 hours and the course of the reaction was monitored by IR spectroscopy. After the educt band at 1840 cm$^{-1}$ in the IR spectrum had vanished, the reaction mixture was cooled. The solvent was distilled off and the reaction mixture was chromatographed over a silica gel column. The by-products were first eluted with acetone, after which the product was eluted with acetone/methanol in a volume ratio of 1:1.

Method (b)

(b) A solution of [A]Rh(μ—CO)$_3$Rh[A] in toluene was exposed to a high pressure mercury lamp (Philips HPK 125) for 6 hours at room temperature. The resulting reaction mixture was worked up as described under 4a).

4.1 [A]RhCO; [A]:[(C$_5$H$_5$)Co[P(O)(OCH$_3$)(O—(CH$_2$)$_3$—CH=CH$_2$)]$_3$]
Preparation according to Method (a):
Substance used: 0.150 g of [A]Rh(μCO)$_3$Rh[A]
Yield: 30%
Preparation according to Method (b):
Substance used: 0.150 g of [A]Rh(μCO)$_3$Rh[A]
Yield: 70%
4.2 [A]RhCO; [A]:[(C$_5$H$_5$)Co[P(O)(OCH$_3$)(O—(CH$_2$)$_6$—CH=CH$_2$)]$_3$]
Preparation according to Method (b):
Substance used: 0.2 g of [A]Rh(μCO)$_3$Rh[A]
Yield: 60%

EXAMPLE 5

Synthesis of [A][Rh(CO)$_2$];
[A]:[(C$_5$H$_5$)Rh(CH$_3$)[P(O)(OCH$_3$)(O—(CH$_2$)$_3$—CH=CH$_2$)]$_3$]$^-$ 0.06 g (0.15 mmol) of [[(CO)$_2$RhCl]$_2$] and 0.164 g (0.3 mmol) of Na[A] were dissolved in 10 ml of dichloromethane. The reaction was complete after 30 minutes (checked by IR). The solution was filtered off from the precipitated sodium chloride and the filtrate was evaporated down. The product, a yellow oil, was formed in a yield of 95%.

The red monocarbonyl complex ([A][Rh(CO)]), which has a characteristic IR band at 1995 cm$^{-1}$, formed slowly from the dicarbonyl complex ([A][Rh(CO)$_2$]) in solution on standing. ([A][Rh(CO)] can be converted back into the dicarbonyl complex by passing in carbon monoxide.

ARh(CO)$_2$, ([A]$^-$32 [(C$_5$H$_5$)Rh(CH$_3$)[P(O)(OCH$_3$)(OCH$_2$CH$_2$CH$_2$CH=CH$_2$)]$_2$]$^-$);
$^1$H—NMR (80 MHz, C$_6$D$_6$); 1.29-1.39(sym.m, RhCH$_3$), 3.33-3.60(virt.m, 6H, 2 POCH$_3$), 3.70-4.10-(sym.m, 4H, 2 POCH$_2$CH$_2$—), 5.15(t,$^3J_{PRhCH}$=2.5 Hz, 5H, C$_5$H$_5$). The resonance signals of the other protons remained unchanged in comparison with the starting compound Na[A] from Example 2.1.

EXAMPLE 6

Cyclotrimerization of dimethyl acetylenedicarboxylate 2.42 g (17.16 mmol) of dimethyl acetylenedicarboxylate, dissolved in 20 ml of toluene, were heated to 120° C., while stirring, in a swinging flask with a reflux condenser. 0.1 g (0.145 mmol) of [(C$_5$H$_5$)CO[P(O)(OCH$_3$)(O(CH$_2$)$_3$—CH=CH$_2$)]$_3$]$_3$$_{Rh(CO),\ dissolved\ in}$ 5 ml of toluene, was added to this solution, as a catalyst. The change in the educt concentration was monitored by gas chromatography. After a reaction time of 24 hours, the yield of hexamethyl mellitate was 51%.

EXAMPLE 7

Hydrogenation of Cyclohexene

For the in situ preparation of the catalyst, 0.07 g (0.1 mmol) of

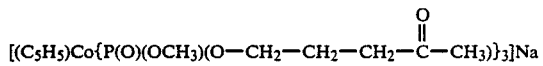

and 0.02 g (0.05 mmol) of [(CO)$_2$RhCl]$_2$ were dissolved in 10 ml of dichloromethane. After 15 minutes, the precipitated sodium chloride was filtered off and the filtrate was used as the catalyst.

This catalyst solution, together with 1000 times the amount of cyclohexene (8.11 g; 0.1 mol), was introduced into a 100 ml stainless steel autoclave. Hydrogen was then forced in until the pressure in the autoclave reached 40 bar. The autoclave was heated at 60° C. for 2 hours, the reaction mixture being stirred. Thereafter, the autoclave was cooled and let down and the reaction mixture was worked up by distillation. Yield: 75%.

EXAMPLE 8.1

Hydroformylation of Alkenes

A solution of 0.1 mmol of the catalyst [(C$_5$H$_5$)Co[P-(O)(OCH$_3$)(O—CH$_2$—CH$_2$—CH$_2$—CH=CH$_2$)]$_3$]Rh-(CO) in 10 ml of tetrahydrofuran was subjected to a pressure of 7 bar with propylene in a 100 ml stainless steel autoclave. Thereafter, hydrogen was forced in to a pressure of 20 bar and carbon monoxide to a pressure of 20 bar. The reaction mixture was heated to 120° C. and the pressure drop was observed. The reaction was complete after 16 hours. The yield of n- and isobutyraldehyde was 71% and the n/iso ratio was 0.56.

EXAMPLE 8.2

The experiment from Example 8.1 was repeated, except that 1 mmol of triphenylphosphine was also added to the reaction mixture. After a reaction time of 16 hours, the yield of n- and isobutyraldehyde was 99% and the n/iso ratio had changed to 1.26.

EXAMPLE 8.3

The experiment from Example 8.1 was repeated, except that the compound [(C$_5$H$_5$)CO[P(O)(OCH$_3$)(O—CH$_2$—CH$_2$—CH$_2$—CN )]$_3$]RH(CO)$_2$ was used as the catalyst and 2.7 mmol of triphenylphosphine were also added to the reaction mixture. The yield of of n- and isobutyraldehyde was 99% after 16 hours. The n/iso ratio had increased under these conditions to 2.01.

EXAMPLE 8.4 (COMPARATIVE EXAMPLE)

This experiment was carried out in order to demonstrate the superiority of the catalytic properties of the novel compounds over the complexes disclosed in the literature and without a functionality F in the phosphonic ester group. The experiment was carried out as in Example 8.1, except that the compound [(C$_5$H$_5$)Co[P(O)(OCH$_3$)$_2$]$_3$]Rh(CO) was used as the catalyst. After a reaction time of 72 hours, the yield of n- and isobutyraldehyde was only 8%.

We claim:

1. transition metal complex of the formula I $$[A]^{x-}[Q]^+{}_x \qquad \text{I}$$

where Q is one equivalent of a cation, x is from 0 to 2 and A is a transition metal complex of the formula

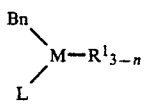

where n is from 1 to 3, M is positively charged cobalt, rhodium, iridium or ruthenium, the groups B are identical or different groups of the formula II

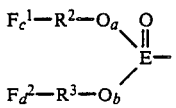

where E is phosphorus or arsenic, O is oxygen, R$^2$ and R$^3$ are each C$_1$-C$_{20}$-alkylene which in turn may carry up to two cycloalkyl, heterocycloalkyl, aryl or hetaryl groups having a total of not more than 15 ring atoms, and R$^2$ and R$^3$ may be interrupted by oxygen, sulfur or (—NR$^4$), R$^4$ is hydrogen or C$_1$-C$_4$-alkyl and the heteroatoms or heteroatom groups are each separated by two or more carbon atoms and the radicals R$^4$ derived from two different (—NR$^4$) groups may furthermore be bonded to one another to form a 5-membered or 6-membered ring, F$^1$ and F$^2$ are each alkenyl, alkynyl, C$_5$-C$_{12}$-cycloalkadienyl, nitrile, amino, C$_1$-C$_4$-mono- and dialkylamino, C$_1$-C$_4$-acyl, hydroxyl, C$_1$-C$_4$-alkoxy, aryloxy, C$_1$-C$_4$-alkylsulfido, arylsulfido, C$_1$-C$_4$-dialkyland and diarylphosphido and/or carboxylato, a-d are each 0 or 1, with the proviso that a+b>0 and c+d>0, L is

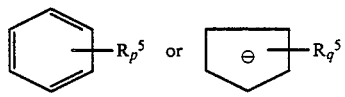

the radicals R$^5$ are identical or different radicals from the group consisting of C$_1$-C$_4$-alkyl and phenyl, p is an integer from 0 to 6 and q is an integer from 0 to 5, and R$^1$ is fluorine, chlorine, bromine, iodine, cyanide, isocyanide, cyanate, isocyanate, thiocyanate, isothiocyanate, C$_1$-C$_4$-alkyl, C$_1$-C$_4$-trialkyl phosphite or triaryl phosphite.

2. A transition metal complex as claimed in claim 1, wherein Q is lithium, sodium, potassium, silver, copper, rhodium, iridium, ruthenium, calcium, magnesium or an ammonium or phosphonium cation.

3. A transition metal complex as claimed in claim 1, which is of the formula III $$[\text{L}-\text{Co}-\text{B}_3]^-[\text{Q}]^+ \qquad \text{III}$$

where E of the group II is phosphorus.

4. A transition metal complex as claimed in claim 1, which is of the formula IV

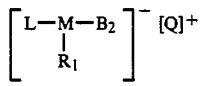

where M is selected from the group consisting of rhodium, iridium and ruthenium cations and E of the group B is phosphorus.

5. A transition metal complex as claimed in claim 1, wherein c is 0 and $R^3$ is $C_1$-$C_{16}$-alkylene.

6. A transition metal complex as claimed in claim 1 of the formula I, where $[Q]^+$ is a complex cation of the type V $$[M^Q Z]^{x\oplus} \qquad \text{V}$$

where X is 1 or 2, $M^Q$ is rhodium, iridium, ruthenium, chromium, tungsten, molybdenum, manganese, rhenium or copper, Z is one of the polydentate ligands $C_7$-cycloalkatriene, $C_5$-$C_{12}$-cycloalkadiene, $C_4$-$C_8$-alkadiene, aryl or a $C_2$-$C_6$-alkylenediphosphido ligand of the formula VI $$R^6\text{—P—}(CH_2)_{1-6}\text{—P—}R^6 \qquad \text{VI}$$

where $R^6$ is $C_1$-$C_4$-alkyl and/or phenyl, and/or from 1 to 3 identical or different ligands selected from the group consisting of the monodentate ligands carbonyl, nitrosyl, chlorine, bromine, iodine, nitrile, isonitrile, $C_1$-$C_4$-alkyl, $C_1$-$C_4$-acyl, $C_1$-$C_4$-alkene, $C_1$-$C_4$-alkyne, $C_1$-$C_4$-trialkylphosphino, triarylphosphino and/or carbyne ligands.

7. A transition metal complex as claimed in claim 1, in which $[Q]^+$ is a complex dication of the formula VII $$[M^Q\text{—K—}M^Q]^{2+} \qquad \text{VII}$$

where the ligands K are from 1 to 3 of the bridging ligands from the group consisting of carbonyl, $C_4$-$C_6$-alkadienyl, $C_8$-$C_{12}$-cycloalkadiene, $C_1$-$C_4$-alkylisonitrile, $C_1$-$C_4$-dialkylphosphido, diarylphosphido and/or $C_1$-$C_6$-alkylenediphosphido ligands of the formula VI.

* * * * *

UNITED STATES PATENT AND TRADEMARK OFFICE
CERTIFICATE OF CORRECTION

PATENT NO. : 4,999,443
DATED : March 12, 1991
INVENTOR(S) : Werner Bertleff, Dieter Koeffer, Wolfgang Klaeui and Choong-Eui Song It is certified that error appears in the above-identified patent and that said Letters Patent is hereby corrected as shown below:

Claim 1, line 1: before "transition", insert the word --A--.

Claim 1, in col. 22, line 32: change "$C_1$-$C_4$-dialkyland" to read -- $C_1$-$C_4$-dialkyl- and --.

Claim 1, in col. 22, line 33: delete "and" (first occurrence).

Signed and Sealed this

Twenty-eighth Day of July, 1992

Attest:

DOUGLAS B. COMER

Attesting Officer    Acting Commissioner of Patents and Trademarks